(12) United States Patent
Ueda (10) Patent No.: US 8,663,237 B2
(45) Date of Patent: Mar. 4, 2014

(54) URETHRA PROTECTION DEVICE (75) Inventor: Tomohiro Ueda, Kyoto (JP)

(73) Assignee: N.M.A. Co., Ltd. (JP)

( * ) Notice: Subject to any disclaimer, the term of this patent is extended or adjusted under 35 U.S.C. 154(b) by 0 days.

(21) Appl. No.: 13/589,674

(22) Filed: Aug. 20, 2012

(65) Prior Publication Data

US 2013/0204089 A1 Aug. 8, 2013

(30) Foreign Application Priority Data

Feb. 3, 2012 (JP) ................................. 2012-021706

(51) Int. Cl.
*A61F 11/00* (2006.01)

(52) U.S. Cl.
USPC ......................................... 606/108; 600/208

(58) Field of Classification Search
USPC ................... 600/121, 208; 606/108
See application file for complete search history.

(56) References Cited

U.S. PATENT DOCUMENTS

| | | | |
|---|---|---|---|
| 5,295,969 A | | 3/1994 | Fischell et al. |
| 5,887,593 A | * | 3/1999 | Levius ........................... 128/885 |
| 6,093,195 A | * | 7/2000 | Ouchi ........................... 606/113 |
| 7,402,141 B2 | * | 7/2008 | Heuser ........................... 600/585 |
| 7,662,145 B2 | * | 2/2010 | Bolmsjo et al. ............... 604/544 |
| 8,282,622 B2 | * | 10/2012 | Dulak et al. ................... 604/523 |
| 8,506,537 B2 | * | 8/2013 | Torstensen et al. ........... 604/264 |
| 2002/0165521 A1 | * | 11/2002 | Cioanta et al. ................ 604/509 |
| 2005/0222581 A1 | * | 10/2005 | Fischer et al. ................ 606/108 |
| 2006/0259120 A1 | * | 11/2006 | Vongphakdy et al. ........ 623/1.11 |
| 2007/0073269 A1 | * | 3/2007 | Becker ........................... 604/509 |
| 2012/0059387 A1 | * | 3/2012 | Schanz et al. ................. 606/108 |

FOREIGN PATENT DOCUMENTS

| | | |
|---|---|---|
| JP | 2000-014663 | 1/2000 |
| JP | 2011-130846 | 7/2011 |

* cited by examiner

*Primary Examiner* — Jason Flick
*Assistant Examiner* — Gerald Landry, II
(74) *Attorney, Agent, or Firm* — Price Heneveld LLP (57) ABSTRACT

It is an object of the present invention to eliminate mechanical stimulation caused by insertion and extraction of such devices as a bladder endoscope and a urethral catheter into and from a urethra. It is a further object of the present invention to make it possible to simultaneously insert such devices as a bladder endoscope and a urethral catheter into the urethra without causing pain. A urethra protection device of the present invention which can be inserted into a urethra includes a first hollow tube in which a bladder endoscope can be inserted, a second hollow tube in which a urethral catheter can be inserted, and a flange provided on an outer peripheral part of the urethra protection device at a position separated from a forward end thereof which is first inserted into the urethra.

18 Claims, 6 Drawing Sheets

URETHRA PROTECTION DEVICE

CROSS-REFERENCE TO RELATED APPLICATIONS

This application claims the benefit of Japanese Application No. JP201221706 filed on Feb. 3, 2012, entitled URETHRA PROTECTION DEVICE, the entire disclosure of which is hereby incorporated by reference.

BACKGROUND OF THE INVENTION

The present invention relates to a urethra protection device. More particularly, the present invention pertains to a urethra protection device which makes it possible to insert a bladder endoscope and a catheter (a urethral catheter) into a urethra without causing pain, the catheter being designed to be inserted into the urethra when in use. The present invention is used chiefly during medical examination or diagnosis of a lower urinary tract disorder, in particular, interstitial cystitis.

SUMMARY OF THE INVENTION

The lower urinary tract disorder is a generic term that refers to anomalies of lower urinary tract functions. Lower urinary tract symptoms caused by lower urinary tract disorders can be classified roughly into three groups: storage symptoms (such as frequent urination and urinary urgency), voiding symptoms (such as dysuria and splitting of urinary stream), and post-urination symptoms (such as feeling of residual urine and post-micturition dribble). The lower urinary tract symptoms also include lower urinary tract pain, such as micturition pain, bladder pain and urethral pain, as well as detrusor overactivity and dysuria, wherein some lower urinary tract disorders are accompanied by hematuria. The lower urinary tract disorders are caused by such diseases as interstitial cystitis, prostatic hypertrophy, prostatitis, prostatism, bladder neck contracture, overactive bladder and bladder pain syndromes.

Various kinds of bladder endoscopes and urethral catheters are publicly known as devices that are used when a subject has, or is suspected of having, a lower urinary tract disorder. These devices are inserted into the urethra for treatment or diagnosis when used. The urethral catheters are available in various shapes and sizes to suit the age and body condition of each patient. Known types of urethral catheters include a catheter usable for injecting a liquid like physiological saline into the bladder as well as a balloon catheter which can be left in a human body when used for an extended period of time. Another known device is a pressure transducer which is used for a urodynamic study.

Among the aforementioned lower urinary tract disorders, interstitial cystitis causes such symptoms as frequent urination, frequent micturition desire, urinary urgency, bladder discomfort and bladder pain. Interstitial cystitis is an intractable disease which does not present a urinary tract infection or other obvious pathological condition and occurs particularly in females. Although interstitial cystitis is a disease of which presence has been recognized only recently, many people, mostly including middle-aged females, suffer from the symptoms of interstitial cystitis. Nevertheless, a definitive diagnostic method of interstitial cystitis has not been established yet and, therefore, bladder hydrodistention under anesthesia which gives severe pain to a patient has conventionally been used.

Under such circumstances, the inventor discovered that an electrode catheter which has never been used for diagnosing interstitial cystitis could be used for this purpose and invented a diagnosis catheter for diagnosing interstitial cystitis which could be inserted into the urethra to diagnose the interior of the bladder, the diagnosis catheter being configured to be connected to a current perception threshold (CPT) inspection apparatus (refer to U.S. Pat. No. 7,338,480).

The inventor carried out a further study of lower urinary tract disorders and discovered that a bladder endoscope system using special light, which has conventionally been limited to use in detecting cancer, could provide a method of detecting angiogenesis in a bladder mucous membrane surface in a lower urinary tract disorder disease such as interstitial cystitis, a painful bladder syndrome or chronic prostatitis with high sensitivity. The inventor then discovered a method of diagnosing interstitial cystitis which is one of the lower urinary tract disorders through comparative observations of a blood vessel and/or a newly formed blood vessel in a surface of a bladder mucous membrane and a blood vessel and/or a newly formed blood vessel in a deep portion of the bladder mucous membrane by using a bladder endoscope system having a special light observation device (refer to U.S. Pat. No. 8,010,185). A method of observing the special light involves narrow band imaging (NBI), auto-fluorescent imaging (AFI) or infrared imaging, for example. Specifically, the electronic endoscope system "EVIS LUCERA SPECTRUM" (registered trademark) manufactured by Olympus Medical Systems Corporation for early detection of cancer can be used for special light observation.

The bladder endoscope and the urethral catheter have conventionally been used in relation to the lower urinary tract disorders as mentioned above and these devices are useful particularly in diagnosing interstitial cystitis, for instance.

Both the bladder endoscope and the urethral catheter inevitably have a drawback, however, in that these devices may come into contact with the urethra and hurt the same when inserted therein or extracted therefrom or used for examination, thereby causing urethral pain or bladder pain. It should be noted additionally that these devices are inserted and extracted a multiple number of times. Furthermore, although the urethral catheter causes pain during insertion and extraction, there may be a case where it is necessary to measure a threshold of pain by use of a CPT inspection apparatus, for example. In such a case, pain caused by catheter insertion/extraction can produce a bias, making it difficult to obtain objectively correct measurement results. Moreover, in a case where it is desired to diagnose or treat a patient with a urethral catheter inserted into the bladder while observing the bladder using a bladder endoscope, it is necessary to insert both the bladder endoscope and the urethral catheter. This would give extremely severe pain to the patient.

Although the lower urinary tract disorders occur in a body portion that is as important as the bladder, there exists no devices that can cope with the aforementioned drawback of the prior art yet. This is due to studies of urothelium being very slow.

In light of the foregoing, it is an object of the present invention to eliminate mechanical stimulation caused by insertion and extraction of such devices as a bladder endoscope and a urethral catheter into and from a urethra. It is a further object of the present invention to make it possible to simultaneously insert such devices as a bladder endoscope and a urethral catheter into the urethra without causing pain and, in particular, to simultaneously insert such devices as a bladder endoscope and a urethral catheter into the urethra without causing pain when diagnosing interstitial cystitis of a female. It is a still further object of the present invention to eliminate such inconvenience as leakage of a liquid from a bladder when injecting physiological saline or the like into the bladder while inserting a bladder endoscope.

To achieve the aforementioned objects, a urethra protection device of the present invention which can be inserted into a urethra includes a first hollow tube in which a bladder endoscope can be inserted, a second hollow tube in which a urethral catheter can be inserted, and a flange provided on an outer peripheral part of the urethra protection device at a position separated from a forward end thereof which is first inserted into the urethra.

Preferably, the urethra protection device is made of a soft, flexible material.

Also, the flange is provided preferably at one end of the urethra protection device that is opposite to an inserting end side thereof.

Also, there is preferably provided a check valve in the first hollow tube.

Also, the check valve is provided preferably at a position separated from the forward end of the urethra protection device.

Also, the check valve is provided preferably at a rear end (i.e., the end opposite to the inserting end side) of the urethra protection device.

Furthermore, the second hollow tube preferably has a diameter not exceeding that of the first hollow tube.

To explain the present invention more specifically, the urethra protection device made of a tubular member including at least a pair of hollow tubes is inserted into the urethra and fixed in position. By making this arrangement in advance, it is possible to subsequently insert and extract such devices as the bladder endoscope and the urethral catheter into and out of the urethra, while ensuring that none of these devices comes into direct contact with the urethra no matter how many times the devices are inserted and extracted. Moreover, the arrangement makes it possible to simultaneously insert a plurality of devices like the bladder endoscope and the urethral catheter. Accordingly, in the present invention, it is not necessarily meant that the first hollow tube can accommodate only the bladder endoscope but that the first hollow tube should have a diameter which is sufficient to permit insertion of at least the bladder endoscope. Similarly, it is not necessarily meant that the second hollow tube can accommodate only the urethral catheter but that the second hollow tube should have a diameter which is sufficient to permit insertion of at least the urethral catheter. According to the present invention, the urethra is protected by the urethra protection device and, therefore, the urethra is not hurt even if an electrode bar is directly inserted, for example. Thus, the present invention provides such an additional advantage that various kinds of elements which could not conventionally be inserted into the urethra can be inserted. As an example, the present invention makes it possible to conduct a urodynamic study while visually recognizing the interior of the bladder by inserting a bladder endoscope and a pressure transducer, for instance. In this invention, it is not meant to exclude the possibility of providing more than two hollow tubes in the urethra protection device. Three or more hollow tubes may be provided as long as the urethra protection device can produce the aforementioned advantages of the invention.

Ureteral fibers presently available for use with the bladder endoscope include those having a diameter of 10 mm or above. Because ureteral fibers whose diameter is approximately 6 mm are also available, however, it is preferable that the first hollow tube has a diameter of 6 mm or above. Furthermore, since finer ureteral fibers are currently under study, the first hollow tube may have a diameter of 2 mm or 3 mm, for example. In essence, the first hollow tube is not limited to a specific range of diameter. Also, since the urethral catheter generally has a diameter of 1 mm to 5 mm which is smaller than the diameter of the bladder endoscope, the second hollow tube preferably has a diameter equal to or smaller than the diameter of the first hollow tube, and more specifically, a diameter of 1 mm to 5 mm. Taking into consideration the fact that the urethra protection device is inserted into the urethra, a portion of the urethra protection device having a maximum diameter excluding the flange preferably has an outer diameter of approximately 5 mm to 20 mm, or equal to or smaller than 5 mm. Also, because the urethra protection device has at least a pair of hollow tubes, the urethra protection device need not necessarily be shaped to have a circular cross section but may take other shapes having, for example, a generally circular cross section which is close to an ellipse.

The above-described structure of the present invention is characterized by the provision of the flange on the outer peripheral part of the urethra protection device. This flange makes it possible to fix the urethra protection device to a human body. Specifically, as the flange rests around the external ureteral orifice, the urethra protection device is kept from being further inserted. Additionally, serving to fix the urethra protection device to the body, the flange prevents friction between the urethra protection device and the body, thereby avoiding undesirable pain. Therefore, the flange is provided at the position separated from the forward end (i.e., the end on the inserting end side) of the urethra protection device at a specific distance therefrom. Taking into consideration the fact that the urethra of a female generally has a length of 3 cm to 6 cm, it is preferable to dispose the flange at a distance of 3 cm to 6 cm from the forward end of the urethra protection device. This means that the urethra protection device should preferably be so structured that the distance from the forward end to the flange is 3 cm to 6 cm. It is pointed out, however, that the location of the flange is not limited to the aforementioned distance since there are individual differences in the length of the urethra. Taking also into consideration ease of design and manufacture, it is preferable to provide the flange at the rear end of the urethra protection device.

Furthermore, since the urethra protection device of the present invention can be fixed to the body by the flange, it is not necessary to make use of a balloon which used to be provided in a urethral catheter for leaving the catheter in the body for an extended period of time. It is therefore possible to configure the urethra protection device to have a smooth tubular shape without surface protrusions and hollows, thereby reducing bodily stimulation.

Although it is not intended to totally disregard the possibility of applications of the present invention to males, the invention produces maximum advantage when used in females who have no prostate but a short urethra and are apt to suffer lower urinary tract disorders (especially interstitial cystitis). In particular, the flange makes it easy to fix the urethra protection device to the perineum and, thus, the provision of the flange is most advantageous for females from this point of view as well. While the flange may be shaped to have a circular cross section or a generally circular cross section along an outer periphery in view of ease of manufacture and use, the flange is not limited to this structure and may be shaped to protrude to both sides of the outer periphery. Specifically, the flange may be configured to have any shape as long as the flange hooks and rests at the external ureteral orifice, thereby accomplishing the purpose of preventing the urethra protection device from being further inserted into the urethra. Also, in actual diagnostic applications, it is possible to easily fix the urethra protection device in a thoroughly acceptable condition by fixing the flange to the perineum by tapes. It will be appreciated from the above that the flange serves an additional function to facilitate fixing of the urethra protection device to the body by means of tapes, for instance. Therefore, thee flange preferably has a width of 5 mm or more, more preferably a width of 10 mm or more. Additionally, the urethra protection device preferably has an outer diameter of 20 mm to 100 mm at a portion where the flange is provided in order to fix the urethra protection device.

Since the urethra protection device is inserted into the urethra when used, the urethra protection device preferably has flexibility similar to a urethral catheter. While materials having flexibility include a hard, flexible material like polytetrafluoroethylene resin, for example, the urethra protection device is preferably made of one of soft, flexible materials, taking into consideration the safety of a living body, the degree of flexibility and ease of use. The soft, flexible materials include, but not limited to, latex rubber (including those coated with silicone or hydrophilic material), thermoplastic elastomer and silicone rubber. Taking, in particular, into consideration a high degree of flexibility, ease of molding, a high degree of safety of a living body, heat resistance and insulation properties, it is particularly preferable to employ silicone rubber.

According to the present invention, there is preferably provided a check valve in the first hollow tube. While the bladder endoscope or the like is inserted in the first hollow tube of the present invention as mentioned in the foregoing discussion, this structure makes it possible to prevent leakage of a liquid from inside the urethra or the bladder when the bladder endoscope or the like is not inserted. Furthermore, it is possible to discharge the liquid, if it is so desired, by inserting another hollow tube into the first hollow tube and opening the check valve, for example.

While it is possible to employ any of such valves as a slit valve, a duckbill valve and a slide valve having various structures'of the prior art as the check valve, it is preferable to use a valve such as a cross-slit valve which does not produce undesirable protrusions and hollows on a peripheral surface of the urethra protection device. Also, taking into consideration ease of manufacture and ease of handling during use, the check valve is provided at a position close to a rear end of the first hollow tube that is separated from the forward end of the urethra protection device, or at the rear end thereof, for example. As will be obviously recognized from the object of the present invention, the check valve serves to prevent an outgoing fluid flow from the bladder.

Provision of a check valve in the second hollow tube is optional. One reason for this is that the second hollow tube preferably has a small diameter of 1 mm to 5 mm as mentioned earlier and, provided that a urethral catheter having the same diameter is inserted in the second hollow tube, liquid leakage will not occur even if no check valve is provided in the second hollow tube. Another reason is that it is possible to easily seal the second hollow tube with a rodlike member or the like without providing a check valve in the second hollow tube.

The present invention featuring the aforementioned structure has the below-described advantages:

The urethra protection device of the present invention, if inserted in the urethra, serves to eliminate mechanical stimulation conventionally caused when a bladder endoscope, a urethral catheter or the like is inserted and extracted into and from the urethra or slid therein. Therefore, neither the bladder endoscope nor the urethral catheter will cause pain even if the bladder endoscope or the urethral catheter is slid in the urethra, or no matter how many times these devices are inserted or extracted.

The urethra protection device of the present invention makes it possible to simultaneously insert a plurality of devices like the bladder endoscope and the urethral catheter and, in addition, to use these devices to examine a patient without producing pain. For this reason, it is possible to eliminate the need to use anesthesia prior to insertion of these devices and shorten insertion time thereof. It is therefore possible to obtain a number of highly objective, precise pieces of diagnostic information at one time.

The urethra protection device of the present invention makes it possible to insert various kinds of devices, other than the bladder endoscope and the urethral catheter, without creating patient burden even if it has conventionally been difficult to insert those devices into the urethra.

Since the urethra protection device of the present invention makes it possible to insert a combination of devices of which insertion into the urethra has conventionally been impossible or extremely difficult without creating patient burden, it is possible to offer the possibility of a new method of diagnosis which has previously been unavailable.

The urethra protection device of the present invention makes it possible to advance a catheter having a small diameter for measuring a current perception threshold by means of a CPT inspection apparatus, for example, up to a target location without causing pain while observing ulcerative and non-ulcerative parts produced by interstitial cystitis with a bladder endoscope. For this reason, it is possible to shorten insertion time and obtain precise pieces of diagnostic information.

As it is possible to easily fix the urethra protection device to a human body by means of the flange, the urethra protection device, once installed, scarcely moves and produces almost no pain.

Even if a liquid such as physiological saline is injected into the bladder with the bladder endoscope inserted therein, it is possible to prevent leakage of the liquid to the exterior by means of the check valve. It is also possible to easily discharge the liquid to the exterior of the body by opening the check valve.

In particular, as a plurality of devices can be inserted into the urethra without pain, it is made possible to conduct a transurethral examination of a female, assist in intermittent catheterization and safely perform bedside examinations. The urethra protection device is also useful as an aid to cystoscopy performed when diagnosing such lower urinary tract disorders as interstitial cystitis, overactive bladder and neurogenic bladder as well as cancer.

DETAILED DESCRIPTION

An embodiment of the present invention is now described with reference to the accompanying drawings.

Figure 1:
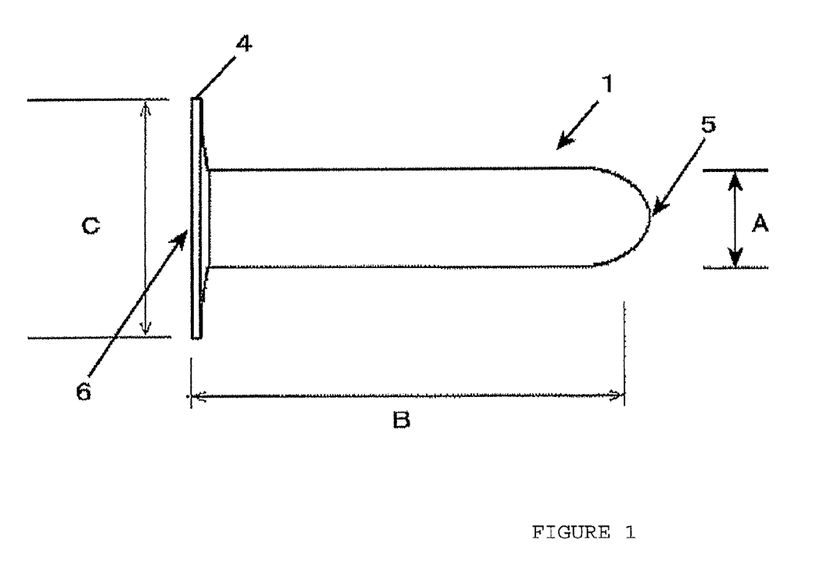
FIG. 1 is a side view of a urethra protection device according to the present invention.
Figure 2:
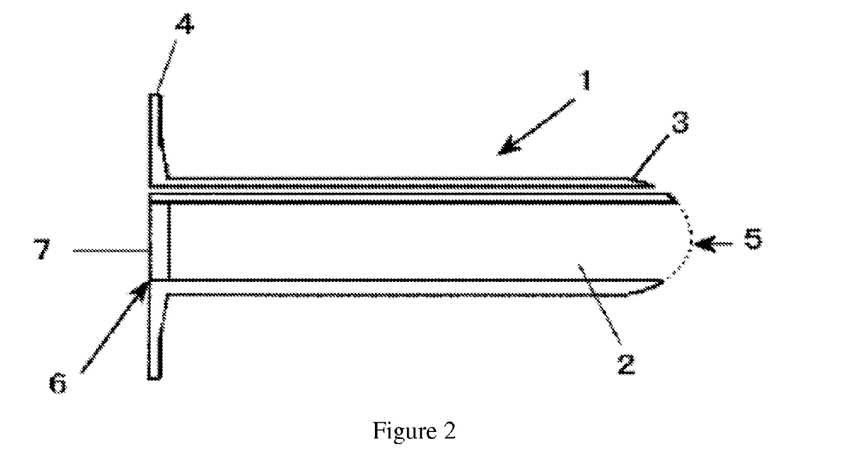
FIG. 2 is a cross-sectional side view of the urethra protection device depicted in FIG. 1.
Figure 3:
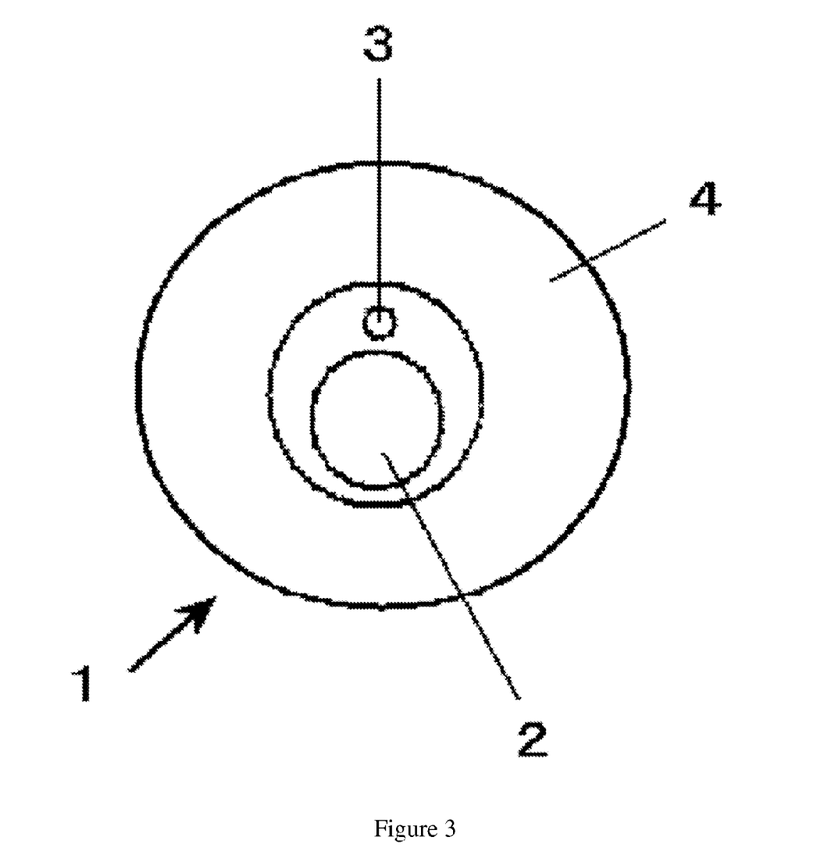
FIG. 3 is a front view of the urethra protection device as seen from an inserting end side depicted in FIG. 1.

FIG. 1 is a side view of a urethra protection device 1 according to the present invention, FIG. 2 is a cross-sectional side view of the urethra protection device 1 depicted in FIG. 1, and FIG. 3 is a front view of the urethra protection device 1 as seen from an inserting end side A depicted in FIG. 1. Each of these Figures is a schematic diagram prepared to facilitate understanding of the present invention. Thus, the Figures are not necessarily drawn to scale and individual elements shown in the Figures do not precisely represent below-mentioned sizes.

As depicted in FIGS. 1 to 3, the urethra protection device 1, which is made of silicone rubber, includes a first hollow tube 2 in which a bladder endoscope 10 (refer to FIGS. 5 and 6) can be inserted, a second hollow tube 3 in which a urethral catheter 11 (refer to FIGS. 4 to 6) can be inserted and a flange 4 provided on an outer peripheral part of a rear end of the urethra protection device 1.

The first hollow tube 2 has a diameter of 5 mm and is so structured that the bladder endoscope 10 can be inserted. The second hollow tube 3 has a diameter of 1 mm and is so structured that the urethral catheter 11 can be inserted. The urethra protection device 1 is structured such that a main portion thereof, excluding the flange 4, has a diameter A of 10 mm. A forward end 5 of the urethra protection device 1 is formed into a rounded shape in side view so that the urethra protection device 1 can be easily inserted into a urethra.

A distance B measured from the forward end 5 of the urethra protection device 1 to the rear end 6 thereof is 40 mm so that the length of the urethra protection device 1 is suited to the average urethra length of a female. The flange 4 provided at the rear end 6 is formed into a generally circular shape along the outer periphery of the urethra protection device 1, the flange 4 having a diameter C of 70 mm.

There is provided a cross-slit valve 7 which serves as a check valve at a position close to the rear end 6 of the first hollow tube 2. The cross-slit valve 7 can prevent leakage of a liquid from the forward end while allowing insertion/extraction of the bladder endoscope 10.

Figure 4:
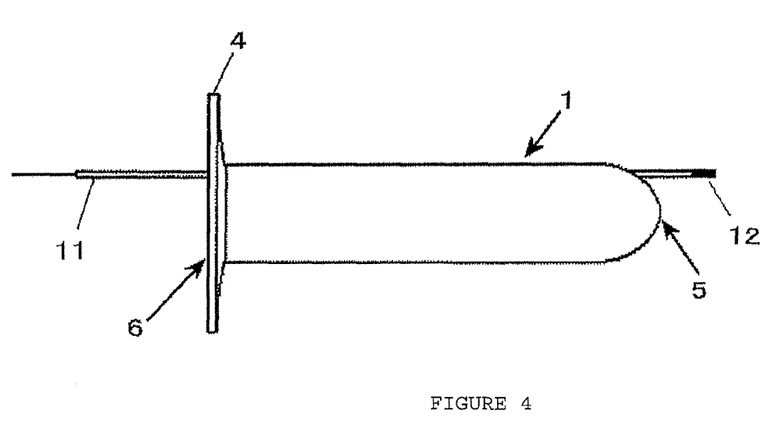
FIG. 4 is a schematic diagram illustrating a state in which a urethral catheter having an electrode has been inserted into the urethra protection device depicted in FIG. 1.

FIG. 4 is a diagram illustrating a state in which the urethral catheter 11 having an electrode 12 has been inserted into the second hollow tube 3 of the urethra protection device 1 depicted in FIG. 1. Since the urethral catheter 11 having the electrode 12 is slidable within the first hollow tube 2 as illustrated, internal examinations of the bladder in a more flexible fashion is made possible. Also, if nothing is inserted in the second hollow tube 3, the second hollow tube 3 serves as a liquid passage which can release a liquid to the exterior. For example, if a rodlike member or the like is inserted in the second hollow tube 3, it is possible to prevent leakage from the second hollow tube 3.

Figure 5:
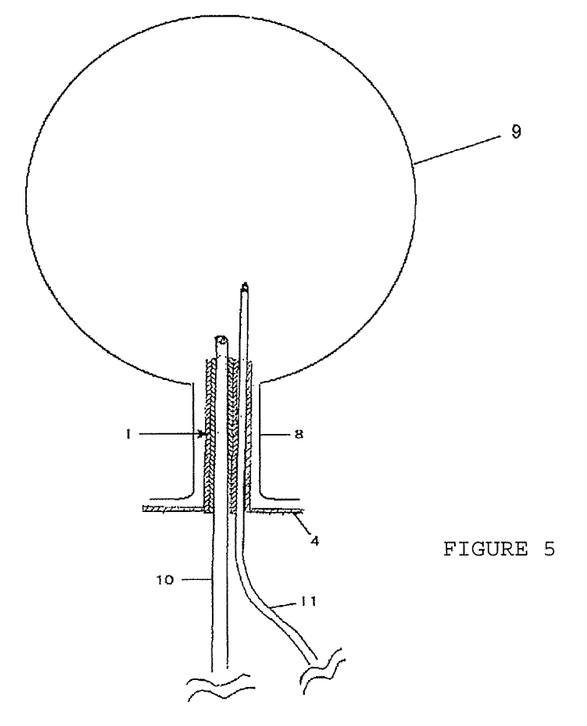
FIG. 5 is a schematic diagram illustrating a state in which the urethra protection device of the present invention is inserted into a urethra of a female.

FIG. 5 is a schematic diagram illustrating a state in which the urethra protection device 1 of the present invention is inserted into a urethra 8 of a female.

The urethra protection device 1 is inserted further into a bladder 9 through the urethra 8 with the forward end 5 of the urethra protection device 1. The urethra protection device 1 is kept from being excessively inserted by the flange 4 and is preferably fixed by tapes 13 (refer to FIG. 6), for instance. It is possible to examine the bladder 9 with the bladder endoscope 10 inserted in the first hollow tube 2 of the urethra protection device 1 and the urethral catheter 11 inserted in the second hollow tube 3. Even if the bladder endoscope 10 and/or the urethral catheter 11 are moved, inserted or extracted during this examination, the urethra protection device 1 ensures that neither the bladder endoscope 10 nor the urethral catheter 11 comes into direct contact with the urethra 8. This makes it possible to eliminate pain caused by friction or the like and perform the examination with increased safety and accuracy without creating undue patient burden.

Figure 6:
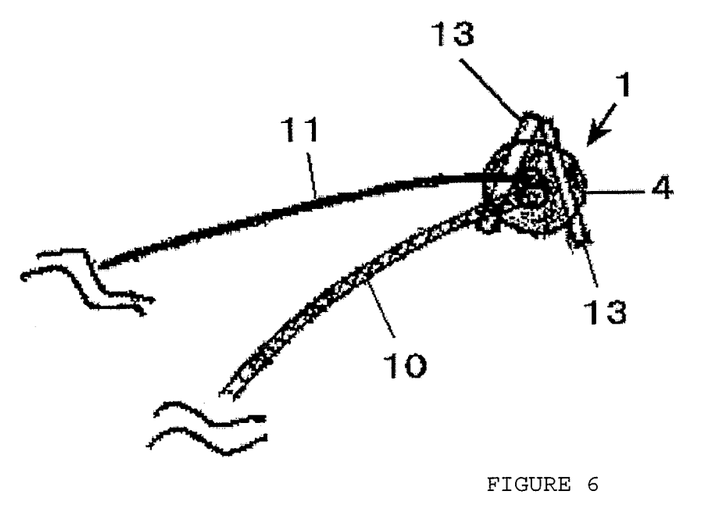
FIG. 6 is a schematic diagram illustrating a state in which the urethra protection device of the present invention is inserted into the urethra of the female and fixed to her perineum by tapes.

FIG. 6 is a schematic diagram illustrating a state in which the urethra protection device 1 of the present invention is inserted into the urethra 8 of the female and fixed to her perineum (not shown) by tapes 13.

More specifically, FIG. 6 is a diagram representing the urethra protection device 1 inserted into the urethra 8 as seen from outside the female body (from outside the female genitalia), wherein neither the legs nor the female genitalia are illustrated. With the bladder endoscope 10 inserted in the first hollow tube 2 of the urethra protection device 1 which is inserted in the urethra 8 and the urethral catheter 11 inserted in the second hollow tube 3, it is possible to examine the bladder 9. The urethra protection device 1 is fixed to the perineum by the tapes 13 from above the flange 4. The flange 4 serves to prevent excessive insertion of the urethra protection device 1 and to ensure that the urethra protection device 1 can be easily fixed to the body by tapes 13 and the like without creating patient burden as described above.

The invention claimed is:

1. A urethra protection device comprising:
    a first hollow tube in which a bladder endoscope can be inserted;
    a second hollow tube in which a urethral catheter can be inserted; and
    a flange configured to allow fixing of the urethra protection device to a perineum, the flange being provided on an outer peripheral part of the urethra protection device at a position separated by 3 to 6 cm from a forward end thereof which is first inserted into the urethra, wherein no protrusions or hollows are present on the outer peripheral part from the flange to the forward end and the urethra protection device is configured for insertion into a urethra of a female, has a tubular shape and is made of a flexible material.

2. The urethra protection device according to claim 1, wherein the forward end is formed to be round in side view and the flange is circular or approximately circular.

3. The urethra protection device according to claim 1, wherein the flange is provided at a rear end of the urethra protection device and wherein the urethra protection device is smooth.

4. The urethra protection device according to claim 2, wherein the flange is provided at a rear end of the urethra protection device and the flange is configured to allow fixing of the device to the perineum using tape affirmed to the flange and perineum.

5. The urethra protection device of claim 1, wherein a check valve is provided in the first hollow tube.

6. The urethra protection device of claim 2, wherein a check valve is provided in the first hollow tube.

7. The urethra protection device of claim 3, wherein a check valve is provided in the first hollow tube.

8. The urethra protection device of claim 5, wherein the check valve is provided at a position separated from the forward end of the urethra protection device.

9. The urethra protection device according to claim 5, wherein the check valve is provided at a rear end of the urethra protection device.

10. The urethra protection device according to claim 1, wherein the second hollow tube has a diameter not exceeding that of the first hollow tube.

11. The urethra protection device according to claim 2, wherein the second hollow tube has a diameter not exceeding that of the first hollow tube.

12. The urethra protection device according to claim 3, wherein the second hollow tube has a diameter not exceeding that of the first hollow tube.

13. The urethra protection device according to claim 4, wherein the second hollow tube has a diameter not exceeding that of the first hollow tube.

14. The urethra protection device according to claim 5, wherein the second hollow tube has a diameter not exceeding that of the first hollow tube.

15. The urethra protection device according to claim 6, wherein the second hollow tube has a diameter not exceeding that of the first hollow tube.

16. The urethra protection device according to claim 7, wherein the second hollow tube has a diameter not exceeding that of the first hollow tube.

17. The urethra protection device according to claim 8, wherein the second hollow tube has a diameter not exceeding that of the first hollow tube.

18. The urethra protection device of claim 1, wherein the urethra protection device is configured to be fixed to a body by the flange without use of a balloon.

\* \* \* \* \*

UNITED STATES PATENT AND TRADEMARK OFFICE
CERTIFICATE OF CORRECTION

| | | |
|---|---|---|
| PATENT NO. | : 8,663,237 B2 | Page 1 of 1 |
| APPLICATION NO. | : 13/589674 | |
| DATED | : March 4, 2014 | |
| INVENTOR(S) | : Ueda | |

It is certified that error appears in the above-identified patent and that said Letters Patent is hereby corrected as shown below:

In the Specification

Column 5, line 4, "thee" should be --the--;

In the Claims

Column 8, claim 4, line 51, "affirmed" should be --affixed--.

Signed and Sealed this
Ninth Day of December, 2014

Michelle K. Lee
*Deputy Director of the United States Patent and Trademark Office*